United States Patent [19]
Toyoda et al.

[11] Patent Number: 5,807,371
[45] Date of Patent: Sep. 15, 1998

[54] EXTENSIBLE TAPE AND ABSORBENT ARTICLE

[75] Inventors: Harumitsu Toyoda; Shinobu Takei, both of Tochigi-ken, Japan

[73] Assignee: Kao Corporation, Tokyo, Japan

[21] Appl. No.: 610,766

[22] Filed: Mar. 5, 1996

[30] Foreign Application Priority Data

Mar. 17, 1995 [JP] Japan .................................. 7-059152
Jul. 28, 1995 [JP] Japan .................................. 7-193662
Nov. 16, 1995 [JP] Japan .................................. 7-298334

[51] Int. Cl.$^6$ .................................................. A61F 13/15
[52] U.S. Cl. ..................... 604/385.1; 604/389; 428/343
[58] Field of Search .......................... 604/385.1, 385.2, 604/386, 389, 390; 428/343, 355 BL, 913

[56] References Cited

U.S. PATENT DOCUMENTS

| | | | |
|---|---|---|---|
| 3,800,796 | 4/1974 | Jacob | 604/385.2 |
| 4,209,016 | 6/1980 | Schaar . | |
| 4,604,096 | 8/1986 | Dean et al. | 604/385.2 |
| 4,778,701 | 10/1988 | Pape et al. | 604/389 |
| 4,787,897 | 11/1988 | Torimae et al. | 604/389 |
| 4,834,820 | 5/1989 | Kondo et al. . | |
| 4,963,140 | 10/1990 | Robertson | 604/389 |
| 5,092,862 | 3/1992 | Muckenfuhs et al. | 604/389 |
| 5,575,784 | 11/1996 | Ames-Ooten et al. | 604/389 |

FOREIGN PATENT DOCUMENTS

| | | | |
|---|---|---|---|
| 0191355 | 8/1986 | European Pat. Off. . | |
| 623330 | 11/1994 | European Pat. Off. | 604/389 |
| 9414056 | 8/1994 | Germany . | |
| 62-15304 | 1/1987 | Japan . | |
| 62-81477 | 4/1987 | Japan . | |
| 3176051 | 7/1991 | Japan | 604/385.2 |
| 89/02728 | 4/1989 | WIPO . | |
| 94/14396 | 7/1994 | WIPO . | |

*Primary Examiner*—Mark O. Polutta
*Attorney, Agent, or Firm*—Birch, Stewart, Kolasch & Birch, LLP

[57] ABSTRACT

An extensible fastening tape includes a base part, adapted to be attached to a disposable absorbent article, and an extensible part attached to the base part, the extensible part being extendable under load of containing the disposable absorbent article.

17 Claims, 11 Drawing Sheets

EXTENSIBLE TAPE AND ABSORBENT ARTICLE

BACKGROUND OF THE INVENTION

1. Field of the Invention

This invention relates to an extensible tape which is suitable for use on disposal absorbent articles, such as disposable diapers, sanitary napkins, and underwear for adults. The present invention is also directed to an absorbent article which can be disposed of sanitarily and easily.

2. Description of Related Art

In recent years, various shorts-type disposable diapers have been proposed. The shorts-type disposable diapers comprise a liquid permeable topsheet, a liquid impermeable backsheet, and an absorbent member interposed between the topsheet and the backsheet. They have a front waist body portion, a rear waist body portion, and a crotch portion disposed in the middle between the front waist body portion and the rear waist body portion. Both side edges of the front waist body portion and both corresponding side edges of the rear waist body portion are joined and sealed together.

Since conventional disposable diapers have no means for securing them, such as with a tape, they cannot be disposed of sanitarily without being fixed with a tape, a rubber band, a string, etc. Such a manner of disposal has been troublesome.

In order to make disposal of shorts-type disposable diapers easier and more sanitary, shorts-type disposable diapers having on the back side thereof a fastening tape in a three-folded state have recently been proposed.

However, the above-mentioned fastening tape in a three-folded state cannot have its entire length, as unfolded, exceed the length of the tape before folding. Therefore, the tape is short in length for fixing a rolled up diaper in some cases, depending on the position of sticking the tape.

In particular, after solid waste materials are discharged, a diaper is usually removed in the following manner. A baby wearing the diaper is laid down and both sides of the diaper are torn apart at the stitches to unfold the diaper. After cleaning the baby's body, there is the tendency that body wipers or tissues used for cleaning are put on the unfolded diaper and the diaper is then rolled up from the front side thereof. For this reason, the fastening tape is usually provided on the back side of a diaper.

When a diaper to be disposed of becomes so bulky due to the excretion of urine and/or feces, tissues, body wipers, etc., the fastening tape is necessarily required to be long. However, the conventional fastening tape fails to fully satisfy such a demand.

In order for shorts-type disposable diapers to have an improved fit so as to prevent them from sliding down and also to improve leakproofness, diapers having gathers in the body-surrounding portion thereof have been proposed. These kind of disposable diapers with their body-surrounding portion gathered produce a problem where the adhesion of the above-described fastening tape is reduced when the tape is attached to the gathered portion. If one tries to stick the fastening tape onto any part except the gathered portion, it sometimes fails because of a shortage in the tape length.

In addition, the above-mentioned disposable diapers are sanitarily unsatisfactory upon disposal of the used diapers. Thus, the waste materials tend to leak from the leg opening portions of the diapers.

Likewise, other absorbent articles, such as sanitary napkins, flat (unfolded) type disposable diapers, pads for incontinence, and underwear for adults, have also been difficult to dispose of using the conventional disposal means. Under the present situation, it has become necessary to provide an absorbent article with a disposal means so that the absorbent article can be disposed of easily, securely, and sanitarily.

SUMMARY OF THE INVENTION

An object of the present invention is to provide an extensible tape suitable as a fastening tape for fastening an absorbent article to be disposed of. The present invention is also concerned with an absorbent article which can be disposed of easily, securely, and sanitarily.

In order to overcome the aforesaid problems, the inventors of the present application have conducted an extensive investigation and have found, as a result thereof, that the above object is accomplished by providing an extensible tape having an extensible part.

The present invention has been completed based on the above finding. The present invention thus provides an extensible tape comprising a base part and an extensible part which is linked with the base part.

The present invention also provides an absorbent article comprising a liquid permeable topsheet, a liquid impermeable backsheet, and an absorbent member interposed between the topsheet and the backsheet, which is characterized in that the topsheet or backsheet has on the surface thereof a strip-shaped fastening tape for fastening the absorbent article together for disposing of the used article. At least a portion of the fastening tape, in its longitudinal direction, is extensible.

The extensible tape according to the present invention is suitable as a fastening tape for fastening an absorbent article together upon disposal of a used absorbent article. The absorbent article according to the present invention can be disposed of easily, securely, and sanitarily.

In more detail, the absorbent article of the present invention can be disposed of easily, securely and sanitarily even when it contains solid waste materials or has absorbed large quantities of urine. In the case that a disposable diaper is used as the absorbent article, even if the diaper has a gathered structure over its entire body-surrounding portion, it can be fastened with the fastening tape without a reduction in the tape adhesiveness. In addition, depending on the constitution of the fastening tape (cf. embodiments shown in FIGS. 10 and 11 described later), a used diaper to be discarded is rolled and fastened through opposing lateral sides of the diaper. In this case, the diaper can also be disposed of sanitarily and easily.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein:

FIG. 3a and 3b provide enlarged views of the fastening tape shown in FIG. 1.

FIG. 7a is an enlarged perspective view (corresponding to FIG. 3b) of a yet another example of the fastening tape which can be used in the present invention in a longitudinally extended condition. FIG. 7b is a schematic view illustrating the condition of a diaper tied with the fastening tape shown in FIG. 7a.

FIGS. 23a, 23b, 23c and 23d provide views illustrating a seventh embodiment of the present invention. FIG. 23b is a cross section of FIG. 23a taken along line b—b of FIG. 23a.

DETAILED DESCRIPTION OF THE EMBODIMENT

The extensible tapes and absorbent articles according to the present invention are explained below by referring to the accompanying drawings. In what follows, while the extensible tapes and absorbent articles will be described with particular reference to absorbent articles having the extensible tape of the present invention, the application of the extensible tape of the present invention is not limited to absorbent articles and can be used as a tape for, for example, wrapping structures for sanitary napkins.

A first embodiment of the shorts-type disposable diaper as an absorbent article according to the present invention is explained by referring to FIGS. 1 through 4.

Figure 1:
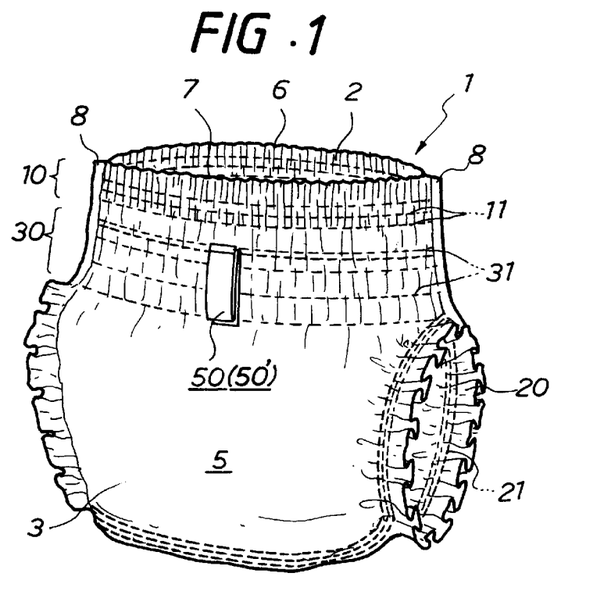
FIG. 1 is a perspective view showing the back side of a shorts-type disposable diaper as one embodiment of the absorbent article according to the present invention.
Figure 2:
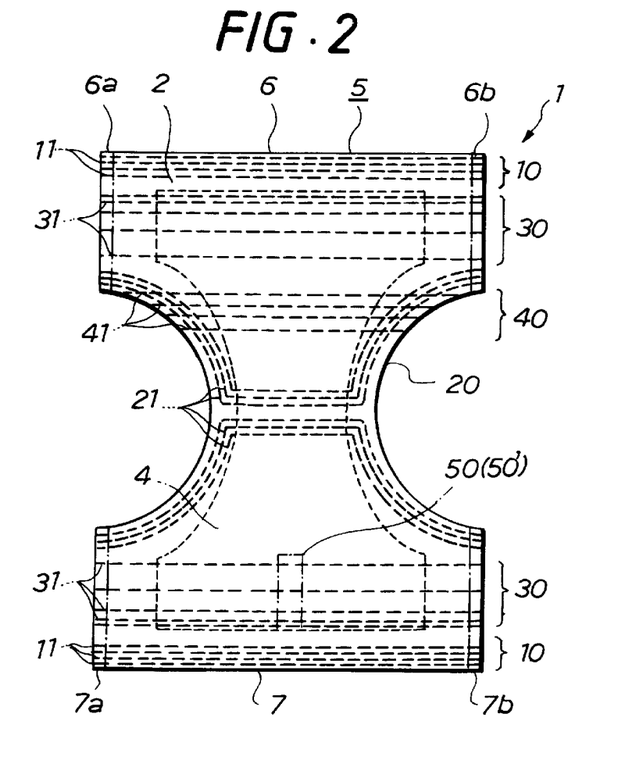
FIG. 2 is a plan view of the disposable diaper shown in FIG. 1 in an unfolded condition.

The shorts-type disposable diaper 1 of this embodiment as shown in FIGS. 1 and 2 comprises an absorbent body 5 having a liquid permeable topsheet 2, a liquid impermeable backsheet 3, and an absorbent member 4 interposed therebetween. Both side edges of the front waist body portion 6 of the absorbent body 5 corresponding to the front waist side of the wearer and those of a rear waist body portion 7 of the absorbent body 5 corresponding to the rear waist side of the wearer are joined and sealed together thereby forming a waist opening portion 10 and a pair of leg opening portions 20. Such a structure is the same as in conventionally known shorts-type disposable diapers.

Going into detail, the side edge 6a of the front waist body portion 6 and the side edge 7a of the rear waist body portion 7 are joined and sealed together, and the side edge 6b of the front waist body portion 6 and the side edge 7b of the rear waist body portion 7 are joined and sealed together, to form a joint 8 on each side thereby forming the shorts.

Elastic members 11 and 21 are provided on the entire peripheral portion of the waist opening portion 10 and the pair of leg opening portions 20, respectively, to form substantially continuous gathered portions. Further, a plurality of elastic members 31 are provided at the body-surrounding portion 30 which is located between the waist opening portion 10 and the pair of leg opening portions 20 and where the absorbent member 4 is provided, to form substantially continuous gathered portions over the entire circumference of the body-surrounding portion 30.

Four elastic members 11 are provided at the waist opening portion 10 of each of the front and rear waist body portions 6 and 7 at regular intervals. The elastic members 11 on the front waist body portion 6 and those on the rear waist body portion 7 are connected and sealed to each other as mentioned above to form substantially continuous gathered portions over the entire circumference of the waist opening portion 10.

Any type of elastic members generally employed in disposable diapers can be used as the elastic member 11 with no particular limitation. The elastic member 11 preferably has a band form.

Three elastic members 21 are provided at the leg opening portion 20 of each of the front and rear waist body portions 6 and 7 at regular intervals and also cross the absorbent member 4 at the bottom portion of the diaper. These elastic members 21 are joined together by the above-mentioned joining and sealing elements to form a substantially continuous gathered portion over-the entire circumference of each leg opening portion 20.

Any of elastic members generally employed in disposable diapers can be used as elastic member 21 with no particular limitation. The elastic member 21 preferably has a band form.

Elastic members are provided at the bottom portion of the diaper by making the above-mentioned elastic members 21 cross the absorbent member 4.

Sealing at the joint 8 is carried out by a known sealing technique, such as heat sealing, radio-frequency sealing, or ultrasonic sealing, with no particular limitation.

As shown in FIG. 2, the shorts-type disposable diaper 1 according to this embodiment has four elastic members 41 at the urination point 40 located below the body-surrounding portion 30 of the front waist body portion 6 and in the vicinity of the urination portion of the wearer, to form continuous gathered portions in the width direction of the diaper.

Any of the elastic members generally employed in disposable diapers can be used as the elastic member 41 with no particular limitation. The elastic member 41 preferably has a string form.

The topsheet 2, backsheet 3, and absorbent member 4 each have a sandglass shape having its central portion narrowed. These members can be formed of the following materials.

The topsheet 2 is made of a liquid permeable sheet which transmits excretions to the absorbent member 4 and preferably feels like underwear. Such a liquid permeable sheet preferably includes woven fabric, nonwoven fabric, and porous film. Leakage of urine, etc. due to oozing from the periphery of the topsheet 2 can be prevented by a water-repellent treatment comprising coating the peripheral portion of the topsheet 2 with a hydrophobic compound such as silicone oil or paraffin wax or coating the entire surface of the topsheet 2 with a hydrophilic compound such as an alkyl phosphate and then washing the peripheral portion with warm water.

Liquid impermeable and vapor permeable sheeting obtained by stretching a filler-containing thermoplastic resin film is used as the backsheet 3. Materials having the feeling of underwear, such as an embossed sheet of the above-described sheeting, a composite material composed of film and nonwoven fabric, and a composite material composed of film and woven fabric, are used.

A combination comprising comminuted pulp as the main component and a water-absorbent high polymer is preferably used as the absorbent member 4. Additionally, a heat-treated mixture of a thermoplastic resin, cellulose fiber or a water-absorbent high polymer is preferred. The water-absorbent high polymer may be present in any of the upper, middle and lower layers and may be present as an admixture with pulp. Water-absorbent high polymers preferably include particles of polymers capable of absorbing and retaining 20 or more times its own weight of liquid and gelling upon liquid absorption. Such water-absorbent high polymers include a saponified starch-acrylic acid (or a salt thereof) graft copolymer, crosslinked sodium carboxymethyl cellulose, and an acrylic acid (or a salt thereof) polymer.

Figure 3A:
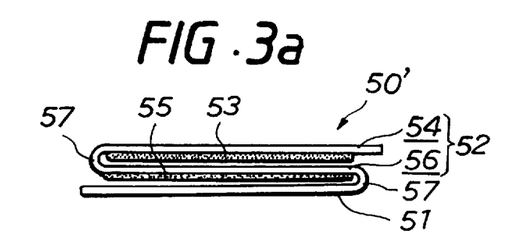
FIG. 3a is an enlarged side view of the fastening tape.
Figure 3B:
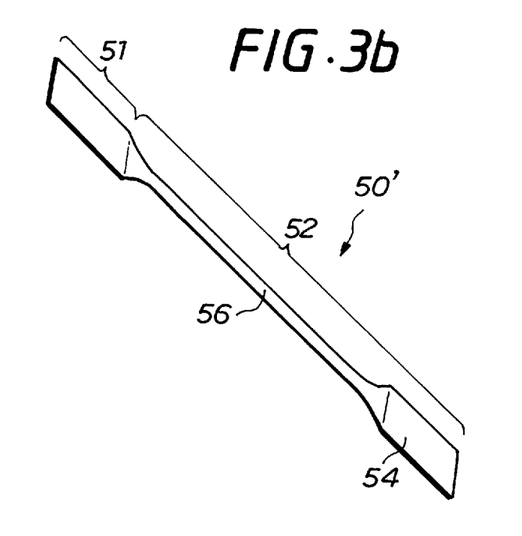
FIG. 3b is an enlarged perspective view of the fastening tape in an extended condition.

As shown in FIGS. 1 and 3, the shorts-type disposable diaper 1 of the present invention has a strip-shaped fastening tape 50 on the outer surface of the backsheet 3. At least a part of the fastening tape 50 is extensible in the longitudinal direction.

In more detail, the fastening tape 50 is provided at about the middle part of the rear waist body portion 7 with its longitudinal direction located in the longitudinal direction of the diaper, as shown in FIG. 1.

The fastening tape 50 comprises an extensible tape 50' as shown in FIGS. 3a and 3b and the extensible tape 50' is fixed at about the central part of the rear waist body portion 7 of the diaper.

The extensible tape 50' according to the present invention which is used as the fastening tape 50 in the diaper of the present embodiment will be described by referring to FIGS. 3a and 3b.

The extensible tape 50' shown in FIG. 3b comprises a base part 51 and an extensible part 56 linked with the base part 51.

In greater detail, as shown in FIG. 3a, the extensible tape 50' is formed by coating a tape substrate with an adhesive, and comprises the base part 51 and the fixing part 52 for fixing the diaper prior to its disposal. A part of the fixing part 52 is extensible in the longitudinal direction of the extensible tape 50' used as the fastening tape 50. The fixing part 52, which is linked with the base part 51 and releasably adhered thereto, comprises the extensible part 56 extensible in the longitudinal direction of the extensible tape 50' and an adhesive part 54 adhering to the backsheet 3 (or topsheet 2) of the diaper. The extensible tape 50' is folded in its longitudinal direction into three layers by two bends 57 (the boundary between the base part 51 and the extensible part 56 and the boundary between the extensible part 56 and the adhesive part 54) at which the tape is divided into approximately equal three parts, and fixed to the surface of the backsheet 3 at the base part 51. The extensible part 56 has a weakly adhesive surface 55, by which it is releasably adhered to the base part 51. The adhesive part 54 has a strongly adhesive surface 53 so that it may be attached to the backsheet 3 (or topsheet 2) of the diaper.

Due to the above-mentioned structure of the extensible tape 50', the extensible part 56 can be extended in the longitudinal direction of the extensible tape 50' through plastic deformation by pulling at the end of the adhesive part 54.

In the extensible tape 50', the base part 51 is preferably formed of such a material that would not undergo plastic deformation under a load of not more than 2000 gf/25 mm, still preferably not more than 3000 gf/25 mm, while the extensible part 56 is preferably formed of such a material that undergoes plastic deformation under a load of not more than 2000 gf/25 mm, still preferably not more than 1000 gf/25 mm.

It is desirable for the base part 51 not to be extended under a load of not more than 2000 gf/25 mm because it is a part that should not be easily extended by the hand. It is desirable for the extensible part 56 to be extended by applying a load of 2000 gf/25 mm or less because it is a part that should be easily extended by hand.

The material for forming the base part 51 and the extensible part 56 which satisfies the above conditions preferably includes resin films prepared by the melt extrusion of polyolefin resins.

Examples of the polyolefin resins include propylene homopolymers; propylene copolymers, such as block, random or random block copolymers of propylene and ethylene; polyblends of the propylene homopolymer and the propylene copolymer; polyethylene, such as high-density polyethylene, low-density polyethylene, and linear low-density polyethylene; and polyblends of the polyethylene and the propylene homopolymer and/or the propylene copolymer. These polyolefin resins may be blended with various thermoplastic elastomers, such as olefins, polyesters, polyamides or styrene elastomers.

The base part 51 may also be formed of the materials generally used in films or sheets, such as polyethylene terephthalate.

In this embodiment, the adhesive part 54 is formed of a material similar to that of the base part 51.

The substrate of the fastening tape disclosed in Japanese Patent Application Laid-Open 62-15304 and Japanese Patent Application Laid-Open 62-285969 can also be used as the extensible tape 50'. The substrate of the disclosed fastening tape comprises an unextensible part (base part) and an extensible part which are integrally formed via a boundary part by the melt extrusion of a polypropylene/polyethylene mixture for the former and a plastic deformable material for the latter.

Further, the fastening tape described in Japanese Patent Application Laid-Open 62-81477 can also be used as the extensible tape 50'. This tape comprises a central part made of an elastic body, such as a general rubber material, and a pair of ends made of a non-elastic body which are connected to the central part. The non-elastic body is formed by impregnating woven fabric and/or nonwoven fabric with an elastic body precursor composition and curing integrally with the elastic body. In addition, a tape prepared by joining a piece of tape made of a plastic undeformable material to each end of a piece of tape made of a plastic deformable material into one body, and a tape comprising a piece of tape made of a plastic deformable material and a plastic undeformable material adhered to the reverse side of each end of the tape may also be employed.

The extensible part 56 preferably has such extensibility that it is extended to 2 to 10 times, still preferably 4 to 6 times, the initial length before extension.

The adhesive for forming the strongly adhesive surface 53 of the extensible tape 50' is preferably a rubber adhesive. Suitable rubber adhesives include hot-melt resins or emulsions, such as a styrene-butadiene block copolymer, a styrene-isoprene block copolymer, an acrylic ester, an acrylic copolymer and vinyl acetate ethylene-vinyl acetate copolymer.

The adhesive for forming the weakly adhesive surface 55 in the fastening tape includes olefin type adhesives. The adhesive for forming a strongly adhesive surface includes rubber adhesives containing a large amount of a petroleum based resin, acrylic adhesives, and rubber adhesives compounded with an addition type silicone.

The extensible tape 50' used as the fastening tape 50 in the disposable diaper of the first embodiment can be produced, for example, as follows.

A plastic deformable material and a plastic undeformable material are used as the tape substrate. The plastic undeformable material is integrally joined to each end of the plastic deformable material via a boundary to provide an extensible tape 50'. An elastic material may be used as the extensible part.

The extensible tape 50' can also be obtained by forming a continuous tape substrate of a plastic deformable material, covering both ends of the substrate with a pair of pieces, and fixing the pieces to both ends of the continuous substrate by heat sealing using a urethane heat sealing compound or by adhering with a hot-melt adhesive so that only the central portion of the substrate undergoes plastic deformation when pulled.

Figure 4:
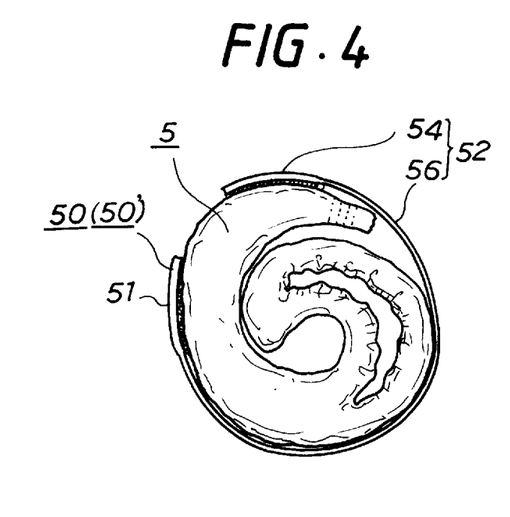
FIG. 4 is a schematic side view illustrating the condition of a shorts-type disposable diaper according to the present invention when it is closed together for disposal.

The shorts-type disposable diaper 1 according to this embodiment can be rolled up and discarded by extending the extensible part 56 of the fastening tape 50 as illustrated in FIG. 3*b*, and sticking the adhesive part 54 to the surface of the rolled diaper as shown in FIG. 4. Instead of being fixed by sticking, the rolled diaper may be tied up with the extended fastening tape.

Since the shorts-type disposable diaper 1 of the present embodiment has the fastening tape 50 which can be extended in the longitudinal direction, it can be fixed in a rolled state easily and securely and be disposed of sanitarily even if it is bulky due to the presence of stools, etc. after excretion or urination. Even where gathered portions are formed all over the body-surrounding portion as with the case of this embodiment, it is possible to extend the fastening tape 50 so as to stick the adhesive part thereof onto any part which does not have gathered portions. Therefore, fastening of the diaper to be disposed of can be conducted with no reduction in adhesiveness of the fastening tape irrespective of whether gathered portions are formed or not.

The shorts-type disposable diapers of the present invention are by no means limited to the aforesaid embodiment, and various alterations can be made without departing from the spirit of the present invention. For example, the following modifications (1) to (4) can be added to the embodiment illustrated in FIGS. 1 to 4.

(1) While the embodiment shown in FIGS. 1 to 4 has been described as an example in which the fastening tape 50 is provided on the surface of the backsheet in the middle part of the rear waist body portion, the fastening tape 50 may be provided on the surface of the topsheet or on the front waist body portion.

Figure 5A:
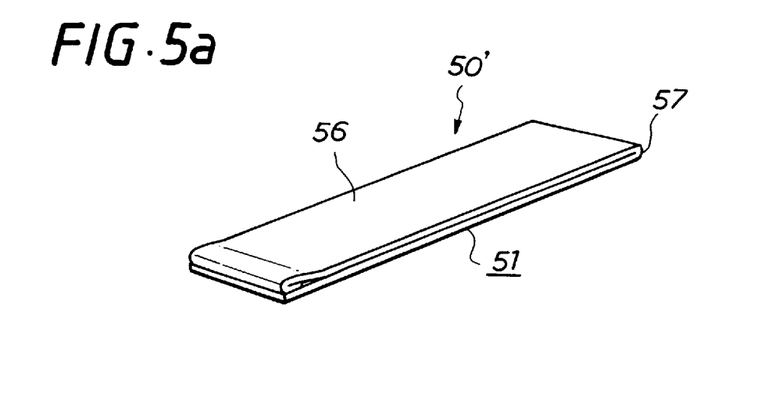
FIG. 5a is a perspective view of another example of the fastening tape which can be used in the present invention.
Figure 5B:
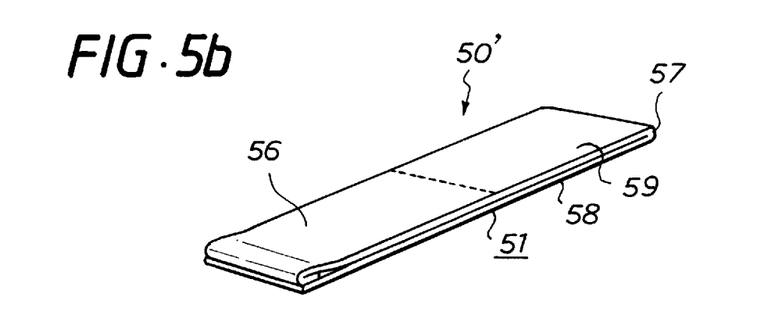
FIG. 5b is a perspective view of still another example of the fastening tape which can be used in the present invention.
Figure 5C:
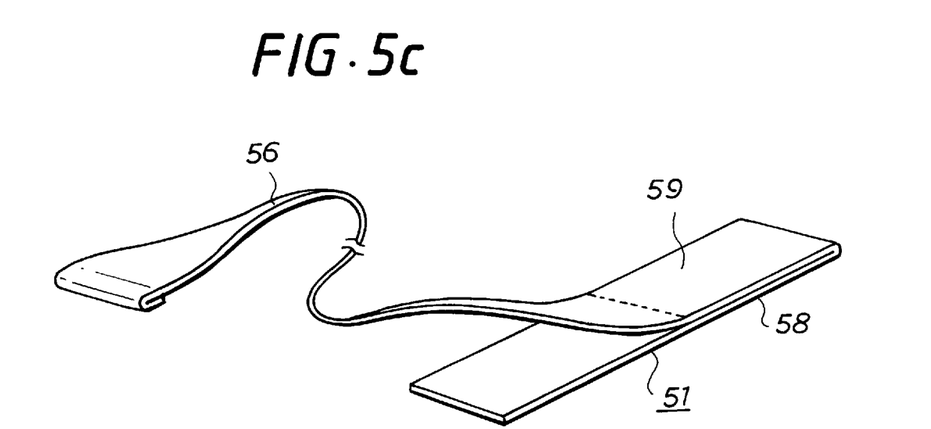
FIG. 5c is an enlarged perspective view (corresponding to FIG. 3b) of the fastening tape shown in FIG. 5b in a longitudinally extended condition.

(2) While the embodiment shown in FIGS. 1 to 4 has been described as an example in which an extensible tape 50' folded into three is provided as the fastening tape 50, the extensible tape may be a tape 50' shown in FIG. 5*a*, in which a tape having a base part 51 and an extensible part 56 linked with the base part 51 is folded in two at a bend 57, and the extensible part 56 is laid on the base part 51; or a Y-shaped tape 50' shown in FIG. 5*b*, in which a base part 51 comprises a fixing part 58 fixed on the backsheet or topsheet and a linking part 59 linked to the fixing part 58, and an extensible part 56 linked with the linking part 59. The tape is folded into two at a bend 57 so that the linking part 59 and the extensible part 56 are laid on the fixing part 58. In the tape shown in FIG. 5*b*, only the front part of the tape portion folded back and overlaid (i.e., the extensible part 56) is extensible as shown in FIG. 5*c*.

Figure 6:
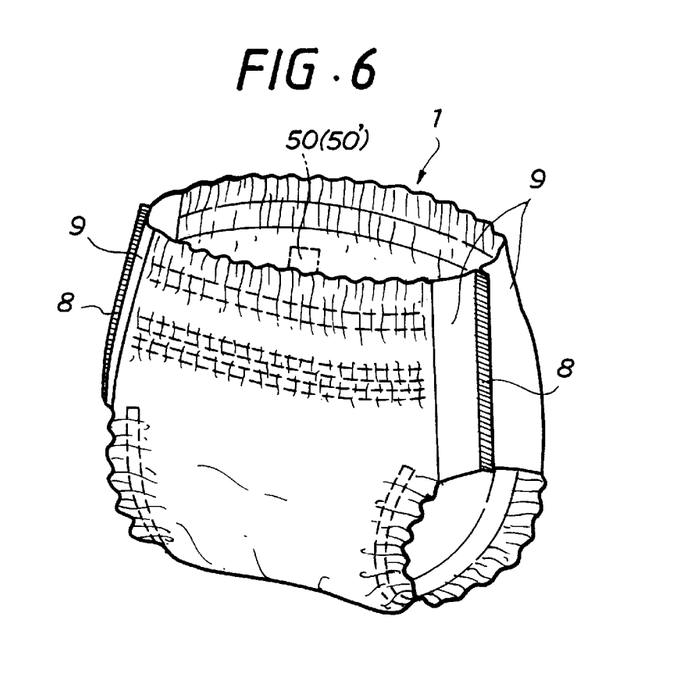
FIG. 6 is a perspective view of another example of the disposable diapers according to the present invention.

(3) The disposable diaper as an absorbent article of the present invention may be of the type shown in FIG. 6. The disposable diaper of FIG. 6 has a stretchable side panel 9 at both side edges of each of the front waist body portion and the rear waist body portion, and the side edges of the side panel 9 are joined and sealed to the side edges of the front and rear waist body portions to form the shape of shorts.

Figures 7A, 7B:
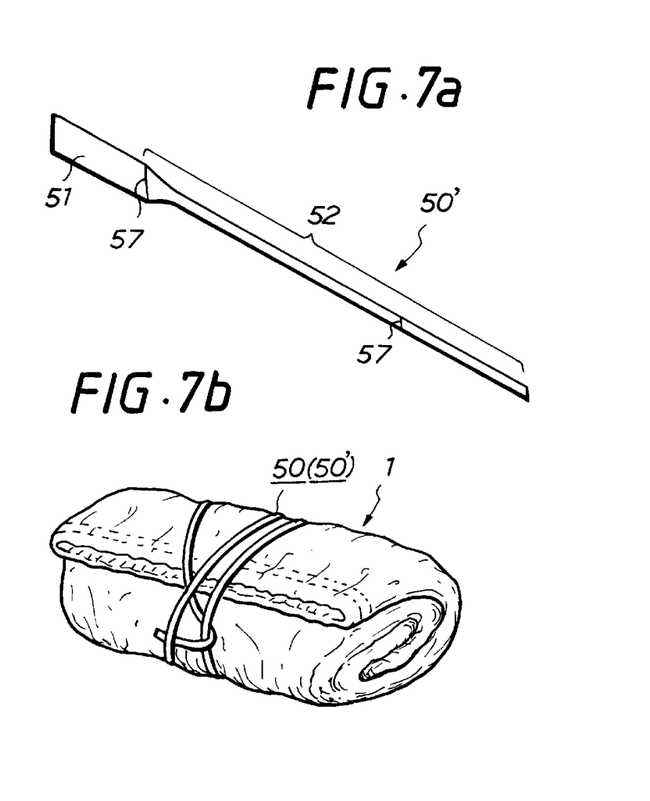

(4) While the embodiment shown in FIGS. 1 to 4 has been described as an example in which the fastening tape 50 has a fixing part 52 in which only a part thereof forms the extensible part 56, the extensible tape 50' may be of the type in which the whole length of the fixing part 52 is the extensible part 56 as shown in FIG. 7a. In using such a fastening tape 50 in which the whole length of the fixing part 52 is extensible, the rolled up diaper can be discarded after being tied up with the tape which is extended like a cord as shown in FIG. 7b.

A second embodiment of the shorts-type disposable diaper as an absorbent article according to the present invention is explained by referring to FIGS. 8 through 12.

Figure 8:
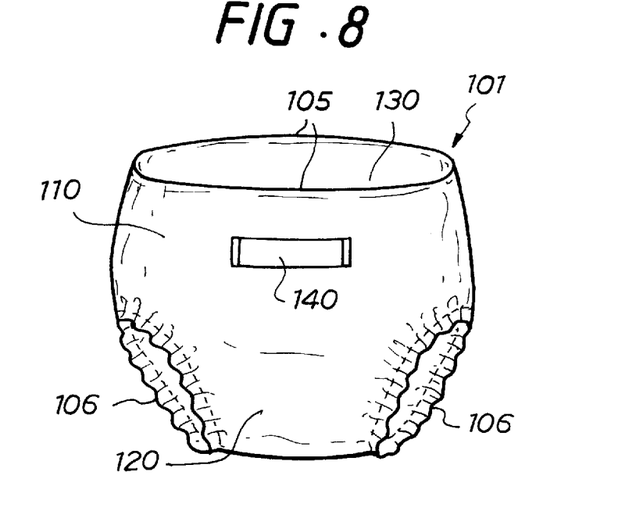
FIG. 8 is a perspective view showing the back side of another embodiment of the shorts-type disposable diapers according to the present invention.
Figure 9:
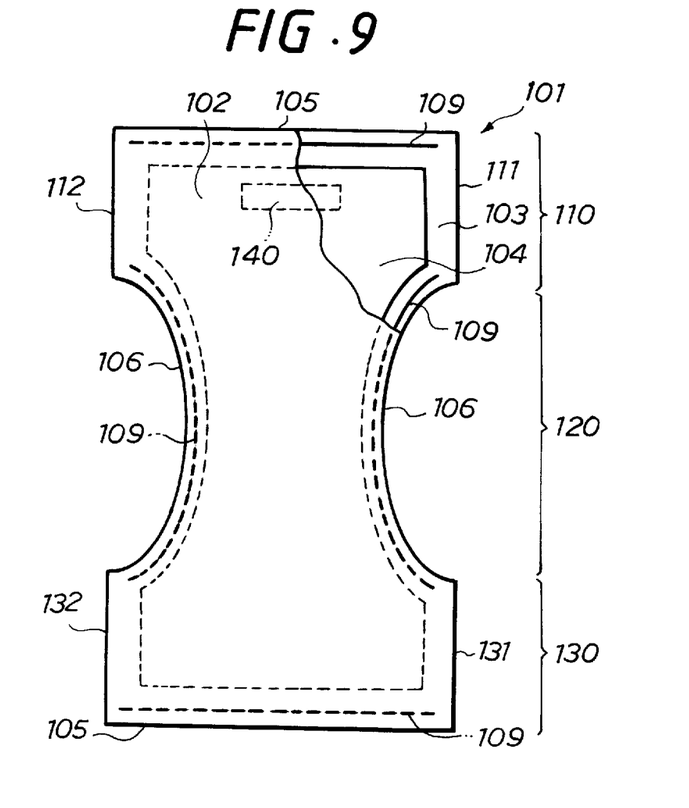
FIG. 9 is a plan view of the disposable diaper shown in FIG. 8 in an unfolded condition.
Figure 10:
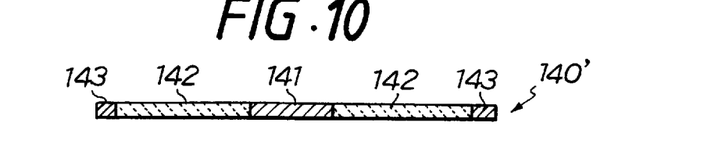
FIG. 10 is an enlarged side view showing the fastening tape of the disposable diaper shown in FIG. 8.
Figure 11:
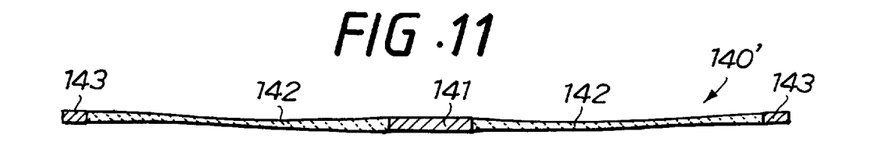
FIG. 11 is a side view of the fastening tape shown in FIG. 10 in a longitudinally extended condition.
Figure 12:
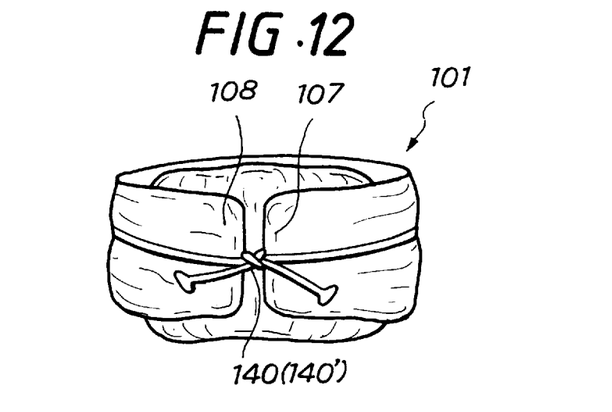
FIG. 12 is a schematic view illustrating the condition of a diaper tied with the fastening tape shown in FIG. 10.

FIG. 8 is a perspective view illustrating the back side of one example of the shorts-type disposable diaper as a second embodiment of the present invention. FIG. 9 is a plan view of the shorts-type disposable diaper shown in FIG. 8 in its unfolded condition. FIG. 10 is an enlarged side view of the extensible tape of the present invention which is used as a fastening tape for a disposable diaper shown in FIG. 8. FIG. 11 is a side view of the extensible tape shown in FIG. 10 in a longitudinally extended condition. FIG. 12 is a schematic view illustrating a diaper which is tied with the fastening tape shown in FIG. 10 and ready for disposal.

As shown in FIGS. 8 and 9, the shorts-type disposable diaper 101 according to the second embodiment comprises a liquid permeable topsheet 102, a liquid impermeable backsheet 103, and an absorbent member 104 interposed therebetween. The diaper 101 has a front waist body portion 130, a rear waist body portion 110, and a crotch portion 120, with both the side edges 131 and 132 of the front waist body portion 130 and both the corresponding side edges 111 and 112 of the rear waist body portion 110 being joined and sealed together. Such a structure is the same as in conventionally known shorts-type disposable diapers.

Going into details, the disposable diaper 101 as unfolded has, as a whole, a sandglass shape with its central portion (crotch portion 120) narrowed.

An elastic member 109 is provided at both side edges of the crotch portion 120, i.e., at a pair of leg opening portions 106, and at a waist portion 105 at the upper and lower edges of the diaper to form gathered portions at the opening portions of the disposable diaper.

The topsheet 102, backsheet 103, absorbent member 104, and elastic member 109 which constitute the disposable diaper 101 can be made of any conventionally known material without particular limitation.

The shorts-type disposable diaper 101 according to this embodiment has a strip-shaped fastening tape 140 for disposal on the surface of the backsheet 103, and at least a part of the fastening tape 140 is extensible in the longitudinal direction.

In more detail, the fastening tape 140 is a strip-shaped tape provided in the width direction of the diaper at about the middle of the rear waist body portion 110. It comprises a base part 141 and a pair of extensible parts 142 which are linked to each end of the base part 141 (see FIGS. 10 and 11).

The fastening tape 140 is provided by fixing an extensible tape 140' shown in FIGS. 10 and 11 at about the middle part of the rear waist body portion 107.

The extensible tape 140' of the present invention which is used as fastening tape 140 in the diaper according to the second embodiment will be explained with reference to FIGS. 10 and 11.

The extensible tape 140' comprises a base part 141 and extensible parts 142 linked to the base part 141.

In greater detail, in the extensible tape 140' the extensible part 142 is linked to each end of the base part 141 in the longitudinal direction, and a pull 143 is provided at the end of each of the extensible parts 142.

The reverse side of the base part 141 is coated with an adhesive (not shown) so it can be fixed onto the surface of the backsheet 103. The reverse side of the extensible parts 142 is coated with an adhesive and releasably stuck to the surface of the backsheet 103.

The material forming the extensible tape 140' is the same as that forming the extensible tape in the first embodiment. The base part 141 and the extensible parts 142 are formed of the same materials forming the base part 51 and the extensible part 56 of the first embodiment, respectively.

The extensible part 142 preferably has such extensibility that it is extended to 2 to 10 times, still preferably 4 to 6 times, the initial length before extension. The length of the extensible part 142 is preferably 1 to 5 cm.

In the extensible tape 140', the adhesive applied to the reverse side of the base part 141 is preferably a rubber adhesive. Suitable rubber adhesives include hot-melt resins or emulsions, such as a styrene-butadiene block copolymer, a styrene-isoprene block copolymer, an acrylic ester, an acrylic copolymer and vinyl acetate ethylene-vinyl acetate copolymer.

In the extensible tape 140', the adhesive applied to the reverse side of the extensible part 142 includes olefin type adhesives, rubber adhesives containing a large amount of a petroleum based resin, acrylic adhesives, and rubber adhesives compounded with an addition type silicone. The adhesive is applied by a coating technique providing a uniform coat at a low spread, such as by melt blowing or slot coating, so that the extensible' part 142 may be temporarily and lightly fixed with little stickiness (releasably stuck to the surface of' the backsheet 103).

The disposable diaper of this embodiment can be disposed of by rolling the diaper, pulling the pulls 143 in the longitudinal direction of the fastening tape 140, rolling both the right and left wings of the diaper inward, and tying the rolled diaper with the extended tape 140 by, for example, knotting, as shown in FIG. 12.

Since the shorts-type disposable diaper according to the present embodiment has a fastening tape having the above-mentioned structure, it can be fixed in a rolled state with its right and left wings also rolled inward like a conventional flat type regular diaper and be disposed of. Accordingly, no leak of excretions from the leg opening portions of the diaper occurs, and the diaper can be rolled more compactly than a conventionally proposed diaper with a tape for disposal and be discarded easily and sanitarily.

Another example of an extensible tape which can be used in disposable diapers according to the present embodiment is explained below by referring to FIGS. 13 to 15.

Figure 13:
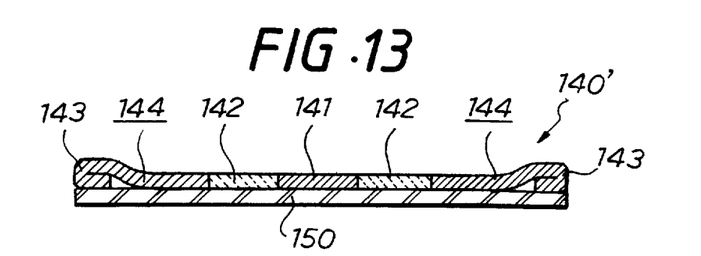
FIG. 13 is an enlarged side view of another example of the fastening tape.

FIG. 13 is an enlarged side view of another example of the extensible tape. FIG. 14 is a side view of the extensible tape shown in FIG. 13 in a longitudinally extended condition. FIG. 15 is a schematic view illustrating a diaper tied with the extensible tape shown in FIG. 13 as it is prepared for disposal.

With respect to the particulars other than those described below, the explanation given to the embodiment shown in FIGS. 8 to 12 applies appropriately.

As shown in FIG. 13, an extensible tape 140' according to this example comprises the above-described extensible parts 142, a fixing part 144 with an adhesive applied to the reverse side thereof (not shown) which is linked to each of the extensible parts 142, and a pull 143 provided at the end of each of the fixing part 144.

The whole fastening tape 140 is fixed to the diaper via a release tape 150 fixed to the diaper.

Going into details, the release tape 150 is fixed on the surface of the backsheet 103 via an adhesive applied to the entire reverse side thereof (not shown). The base part 141 in the fastening tape 140 is fixed to the surface of the release tape 150, whereby it is fixed to the diaper via the release tape 150. The extensible parts 142 and the fixing parts 144 are releasably stuck to the surface of the release tape 150.

Each of the pulls 143 is formed by turning the tip of the fixing part 144 back on itself to the reverse side thereof. The fixing part 144 is formed of the same material in the same manner as for the above-described base part 141. The part of the release tape 150 in contact with the base part has no release properties, whereby the base part 141 is fixed to the release tape 150, while the fixing part 144 is releasably adhered to the release tape 150.

Any release tape that has been used in conventional sanitary goods, such as absorbent articles like disposable diapers, can be used as a release tape 150 with no particular restriction.

Figure 14:
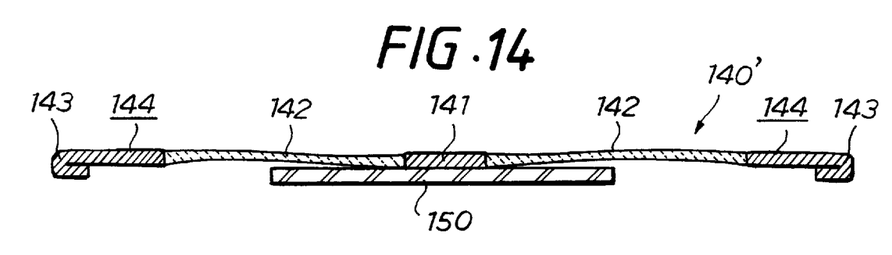
FIG. 14 is a side view of the fastening tape shown in FIG. 13 in a longitudinally extended condition.
Figure 15:
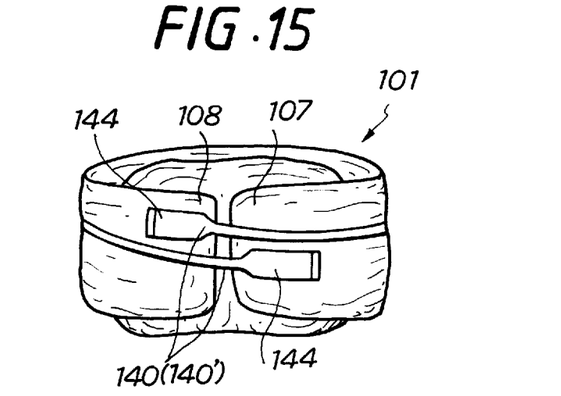
FIG. 15 is a schematic view illustrating the condition of a diaper tied with the fastening tape shown in FIG. 13.

When the disposable diaper of this embodiment using the extensible tape 140' as fastening tape is disposed of, the diaper is rolled, the fastening tape 140 is pulled at the pulls 143 in the longitudinal direction of the fastening tape 140 to extend the extensible parts 142 as shown in FIG. 14, both the right and left wings of the diaper are rolled inward, and the rolled diaper is tied with the extended fastening tape 140 by, for example, sticking the fixing parts 144 to the surface of the diaper as shown in FIG. 15. The diaper can thus be discarded sanitarily and easily.

A third embodiment of the shorts-type disposable diapers as an absorbent article according to the present invention is explained by referring to FIGS. 16 through 19.

Figure 16:
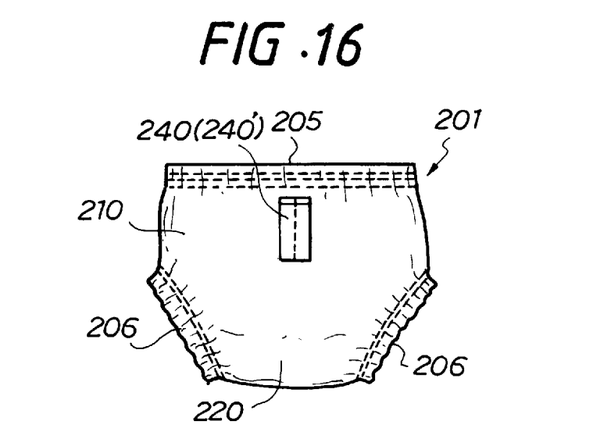
FIG. 16 is a back side view of a shorts-type disposable diaper according to a third embodiment of the present invention.
Figure 17:
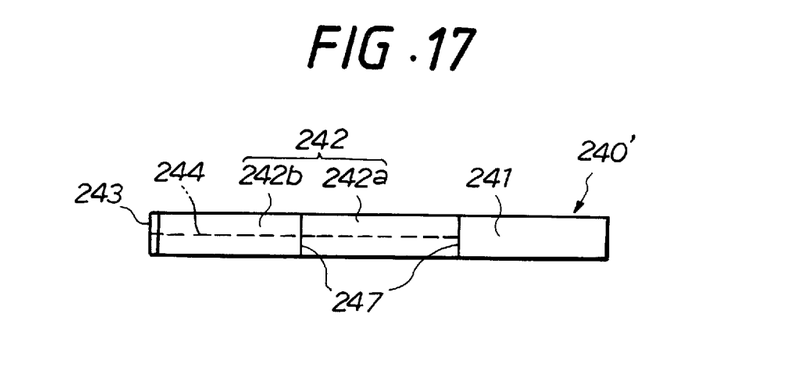
FIG. 17 is a plan view of the extensible tape according to the present invention which is used as a fastening tape of the shorts-type disposable diaper shown in FIG. 16.
Figure 18:
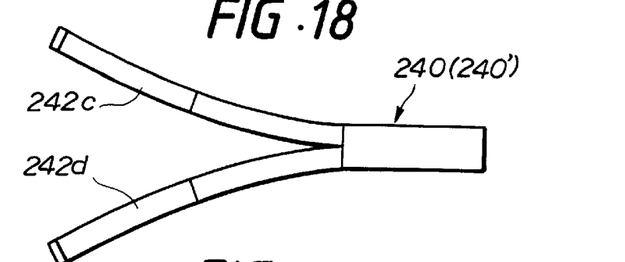
FIG. 18 is a plan view showing the extensible tape shown in FIG. 17 in a separated condition.
Figure 19:
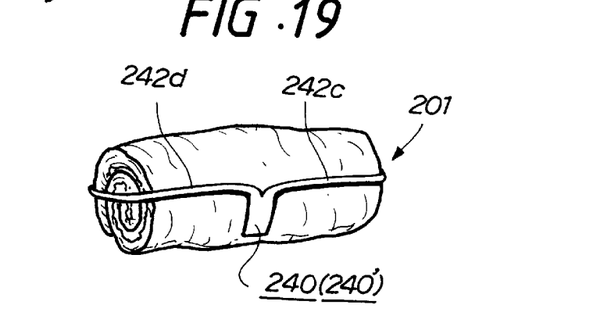
FIG. 19 is a schematic view illustrating the condition of a diaper tied with the fastening tape shown in FIG. 18.

FIG. 16 is a back side view of a shorts-type disposable diaper according to the third embodiment of the present invention. FIG. 17 is a plan view of the extensible tape according to the present invention which is used as the fastening tape for the shorts-type disposable diaper shown in FIG. 16. FIG. 18 is a plan view showing the extensible tape shown in FIG. 17 in a separated condition. FIG. 19 is a schematic view illustrating the condition of a diaper fixed with the fastening tape shown in FIG. 18.

The disposable diaper 201 of this embodiment shown in FIG. 16 is formed in practically the same manner as for the shorts-type disposable diaper of the second embodiment. So, the diaper of the third embodiment will be explained only as for the points different from the diaper of the second embodiment, with the explanation on the same points omitted. Accordingly, with respect to the particulars other than those described below, the explanation given to the second embodiment applies herein as appropriate.

The disposable diaper 201 shown in FIG. 16 has, on the surface of the backsheet, a strip-shaped fastening tape 240 to be used for disposal, and at least a part of the fastening tape 240 is extensible in the longitudinal direction thereof.

In more detail, the fastening tape 240 is provided at about the middle portion of the rear waist body portion 210 along the longitudinal direction of the diaper.

The fastening tape 240 is provided by fixing an extensible tape 240' of the present invention shown in FIGS. 17 and 18 at about the middle part of the rear waist body portion.

The extensible tape 240' used as a fastening tape 240 of the diaper according to this embodiment is explained below by referring to FIGS. 17 and 18.

The extensible tape 240' shown in FIG. 17 comprises a base part 241 and an extensible part 242 linked to the base part 241.

In more detail, as shown in FIG. 17 the extensible tape 240' is folded in its longitudinal direction into three sections with two bends 247 at which the extensible tape 240' is divided into approximately equal three parts to form a base part 241 and extensible parts 242a and 242b which are extensible in the longitudinal direction of the extensible tape 240'. The extensible parts 242a and 242b are linked to the base part 241 and releasably adhered to the base part 241. The tip of the extensible part 242b is turned back to form a pull 243.

The extensible parts 242a and 242b have a weak adhesive surface (not shown), with which the extensible part 242a is releasably adhered to the base part 241, and the extensible part 242a to the extensible part 242b, respectively. As the adhesive which provides the weak adhesive surface, the above-mentioned adhesives used for the extensible tape shown in FIGS. 3 and 4 can be used as appropriate.

The extensible parts 242a and 242b have perforations 244 along a centerline in the width direction. When the extensible parts 242a and 242b are released and extended (unfolded) by pulling at the pull 243, they are separated into a left-hand part 242c and a right-hand part 242d.

Being extensible, both the left-hand part 242c and the right-hand part 242d can be extended in the longitudinal direction.

The materials constituting the extensible tape 240' and the process' for producing the extensible tape 240' are the same as those for the extensible tapes used in the second embodiment.

The extensible part 242 preferably has such extensibility that it can be extended to 2 to 10 times, still preferably 4 to 6 times, the initial length before extension.

The disposable diaper of this embodiment can be disposed of by rolling up the diaper, pulling the left-hand part 242c and the right-hand part 242d by the pull 243 in the longitudinal direction of the fastening tape 240, rolling both the right and left wings of the diaper inward, and tying the rolled diaper with the extended left-hand part 242c and right-hand part 242d by, for example, knotting, as shown in FIG. 19.

The fourth embodiment of the absorbent articles according to the present invention will be explained by referring to FIG. 20.

Figure 20:
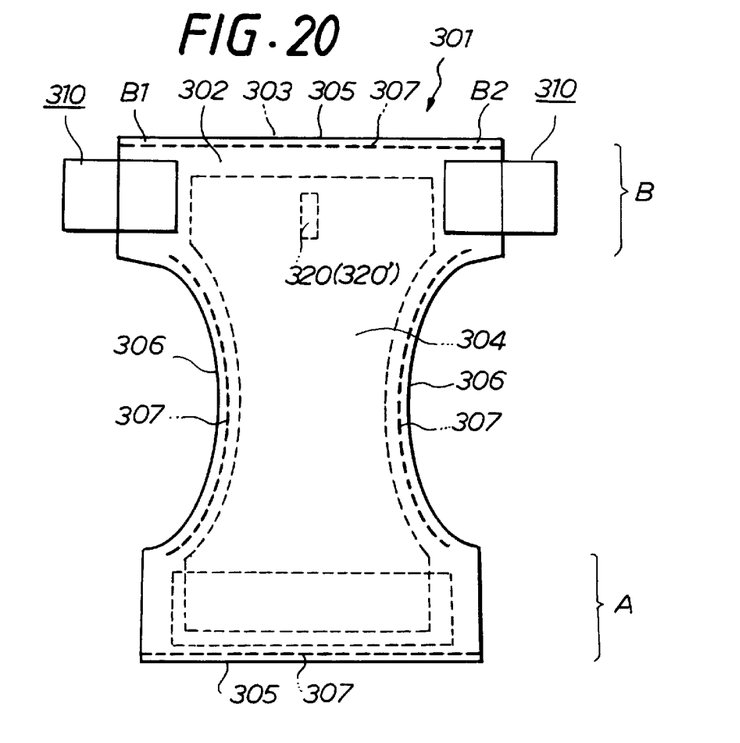
FIG. 20 is a plan view of a flat (unfolded) type disposable diaper as a fourth embodiment of the absorbent articles according to the present invention.

FIG. 20 is a plan view of a flat type disposable diaper as a fourth embodiment of the absorbent articles according to the present invention in its unfolded condition.

As shown in FIG. 20, the absorbent article of the fourth embodiment comprises a liquid permeable topsheet 302, a liquid impermeable backsheet 303, and an absorbent member 304 interposed therebetween. It is a flat (unfolded) type diaper having a front waist body portion A corresponding to the front waist side of a wearer and a rear waist body portion B corresponding to the rear waist side of a wearer, with a pair of fastening tape 310 being provided at both the side edges B1 and B2 of the rear waist body portion B for fastening the diaper while it is worn. Such a structure is the same as conventionally known flat type disposable diapers.

Going into details, as shown in FIG. 20, the disposable diaper 301 according to this embodiment has its absorbent member 304 narrowed at the crotch portion thereof to have a sandglass shape, and the topsheet 302 and the backsheet 303 are also narrowed at the crotch portion, following the shape of the absorbent member 304. The absorbent member 304 is held and fixed between the topsheet 302 and the backsheet 303. A waist portion 305 and leg portions 306 at the periphery of the absorbent member 304 are provided with an elastic stretchable member 307 for fitting the waist portion 305 and the leg portions 306 to a wearer's body, as sandwiched in between the topsheet 302 and the backsheet 303. Conventionally employed materials can be used for forming the topsheet 302, backsheet 303, absorbent member 304 and elastic stretchable member 307 with no particular restriction.

In the disposable diaper 301 of the present embodiment, a fastening tape 320 is provided along the longitudinal direction of the diaper at about the middle part of the rear waist body portion B in the width direction. The fastening tape 320 is the same as the extensible tape of the present invention shown in FIGS. 3 and 4 which is used in the first embodiment.

The fifth embodiment of the absorbent articles according to the present invention will be described by referring to FIG. 21.

Figure 21:
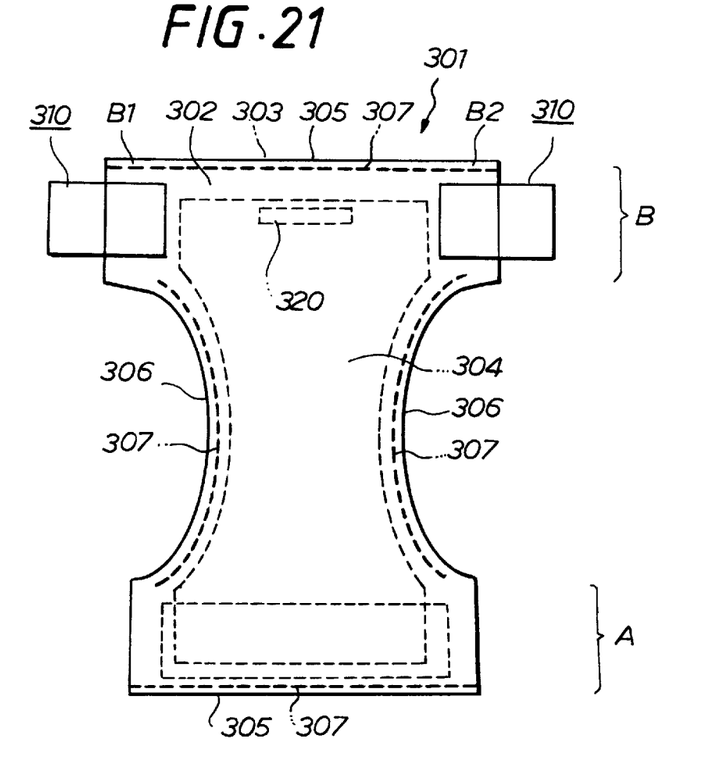
FIG. 21 is a plan view of a flat type disposable diaper as a fifth embodiment of the absorbent articles according to the present invention.

FIG. 21 is a plan view of a flat type disposable diaper as a fifth embodiment of the absorbent articles according to the present invention in its unfolded condition.

Because the disposable diaper according to this embodiment is substantially the same as that of the fourth embodiment, explanation will be given only to the different points. Accordingly, with respect to the particulars other than those described below, the explanation given to the fourth embodiment can be applied as appropriate.

The absorbent article of the fifth embodiment has a fastening tape 320 extending in the width direction of the diaper at about the middle part of the rear waist body portion. The fastening tape 320 is the same as the extensible tape of the present invention shown in FIGS. 10 and 11 which is used in the second embodiment.

The sixth embodiment of the absorbent articles according to the present invention will be explained with reference to FIG. 22.

Figure 22:
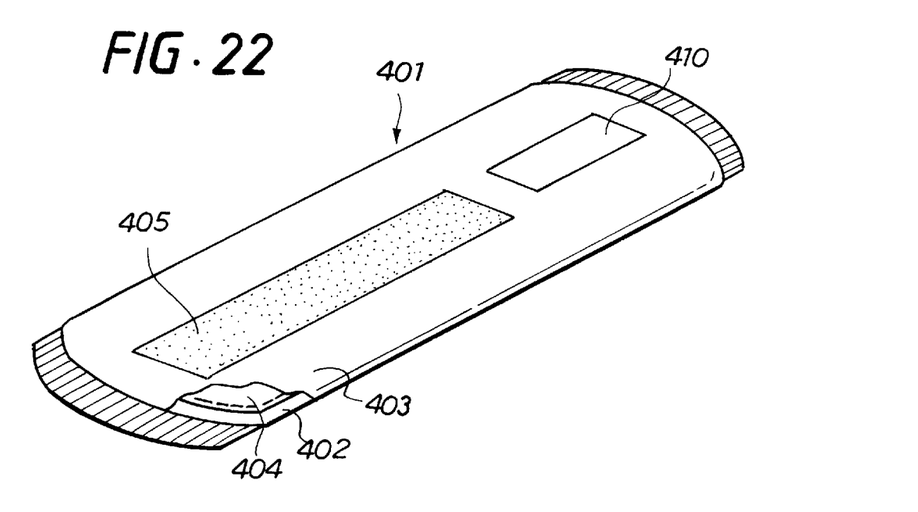
FIG. 22 is a perspective view illustrating a sanitary napkin as a sixth embodiment of the absorbent articles according to the present invention, with a part thereof cut away.

FIG. 22 is a plan view of a sanitary napkin as a sixth embodiment of the absorbent articles according to the present invention.

As shown in FIG. 22, a sanitary napkin 401, which can have a substantially rectangular shape, comprises a liquid permeable topsheet 402, a liquid impermeable backsheet 403, and an absorbent member 404 interposed between the topsheet 402 and the backsheet 403. Such a structure is the same as conventional sanitary napkins.

An adhesive is applied to the surface of the backsheet 403 to provide a fixing part 405 for prevention of sliding during use.

Conventionally known materials can be used for the topsheet 402, backsheet 403, absorbent member 404, and the above-described adhesive with no particular limitation.

In the sanitary napkin according to this embodiment, a fastening tape 410 is provided on one end of the backsheet 403 along the longitudinal direction of the sanitary napkin.

The fastening tape 410 is the same as the extensible tape of the present invention shown in FIGS. 3 and 4 which is used in the first embodiment.

The seventh embodiment of the present invention is then explained by referring to FIGS. 23a, 23b, 23c and 23d.

Figure 23A:
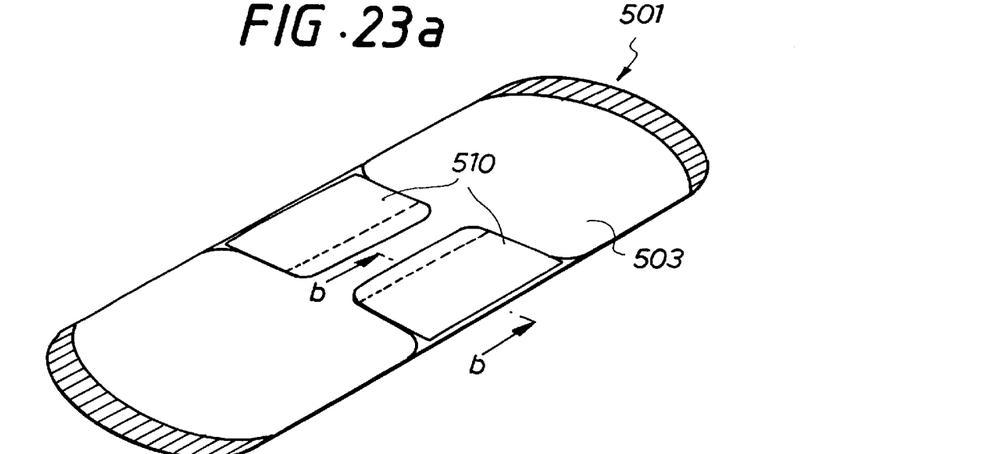
FIG. 23a is a perspective view showing the backsheet side of a sanitary napkin according to this embodiment.
Figure 23B:
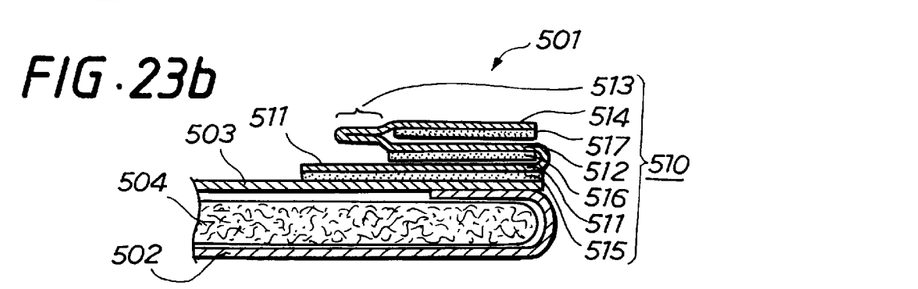
Figure 23C:
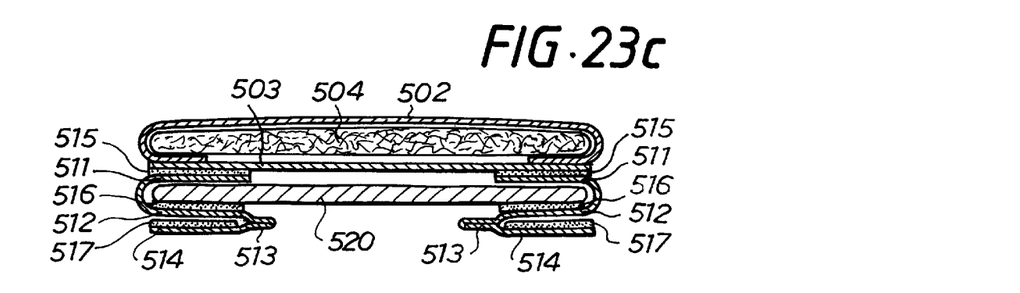
FIG. 23c is a cross section of the sanitary napkin shown in FIG. 23a in its width direction and in a condition as applied to underwear.
Figure 23D:
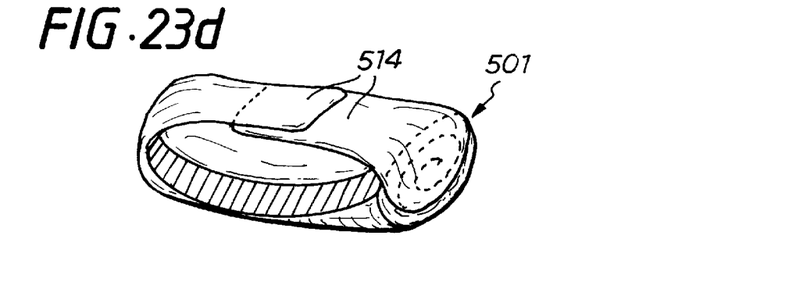
FIG. 23d is a perspective view illustrating the napkin in a disposable condition.

FIGS. 23a, 23b, 23c and 23d provide views illustrating the seventh embodiment of the present invention. FIG. 23a is a perspective view showing the backsheet side of the sanitary napkin according to this embodiment. FIG. 23b is a cross section of FIG. 23a taken along line b—b of FIG. 23a. FIG. 23c is a cross section of the sanitary napkin in its width direction in a condition applied to underwear. FIG. 23d is a perspective view illustrating the napkin ready for disposal.

As shown in FIGS. 23a and 23b, a sanitary napkin 501, having a rectangular shape according to this embodiment comprises a liquid permeable topsheet 502, a liquid impermeable backsheet 503, and an absorbent member 504 interposed between the topsheet 502 and the backsheet 503. A pair of wings 510 for fixing the napkin to underwear are provided at the middle of the backsheet 503 in the longitudinal direction of the napkin. Such a structure is the same as conventional sanitary napkins.

In the sanitary napkin 501 according to this embodiment, the wings 510 are formed of the extensible tape of the present invention.

That is, as shown in FIG. 23b, each of the wings 510 comprises a base part 511 fixed to the backsheet 503 of the napkin, an extensible part 512 linked to the base part, and a fixing part 514 linked to the extensible part 512 via a pull 513.

The extensible part 512 is folded on the base part 511, and the fixing part 514 is folded on the extensible part 512. On the folded surface of each of the base part 511, extensible part 512, and fixing part 514 is applied an adhesive 515, 516, and 517, respectively. The surface of the base 511 (the side in contact with the adhesive 516) is a release surface, as is the surface of the extensible part 512 (the side in contact with the adhesive 517).

The pull 513 is formed by directly bonding the tip of the extensible part 512 and the tip of the fixing part 514. The pull 513 may be colored to improve handling properties when in use.

In use, the sanitary napkin 501 of this embodiment is fixed to underwear (panties) by releasing the extensible part 512 from the base part 511 at the pull and sticking the adhesive 516 of the extensible part 512 to panties 520 as shown in FIG. 23c. After use, the napkin 501 is rolled up, the extensible part 512 is extended, and the fixing part 514 is fixed to an appropriate position. The napkin 501 can thus be disposed of sanitarily in a rolled state as shown in FIG. 23d.

The absorbent articles according to the fourth to seventh embodiments can be disposed of after use by easy handling and in a sanitary way in the same manner as the absorbent articles of the first and second embodiments.

The absorbent articles of the present invention are not limited to the aforesaid embodiments, and various changes and modifications can be made without departing from the spirit of the present invention.

Figure 24:
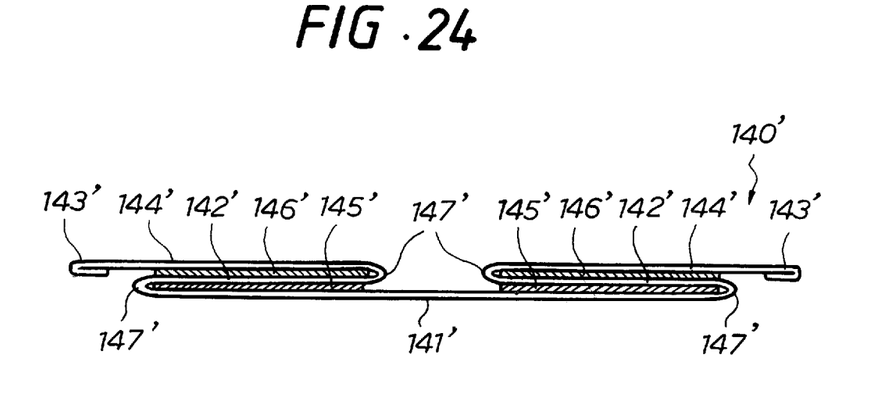
FIG. 24 is an enlarged side view illustrating another example of the extensible tape according to the present invention.

For example, the extensible tape 140 used in the second embodiment can be replaced with an extensible tape 140' shown in FIG. 24. The extensible tape 140' shown in FIG. 24 comprises a base part 141', an extensible part 142' linked to each end of the base part 141', and an adhesive part 144' linked to the extensible part 142'. A pull 143' is provided at the end of both the right and left ends. Each of the right and left sides of the extensible tape 140' is folded into three at bends 147' in such a manner that the extensible part 142' and the adhesive part 144' are overlaid on the base part 141' in this order.

A weakly adhesive surface 145' is formed on the reverse side of the extensible part 142', while a strongly adhesive surface 146' is formed on the reverse side of the adhesive part 144'. The extensible part 142', base part 141', adhesive part 144', weakly adhesive surface 145', and strongly adhesive surface 146' are made of the same materials as used in the extensible tape-50' of the first embodiment.

On disposal, pulls 143' which are provided at both ends of the extensible tape 140' in the same manner as in the tape shown in FIGS. 13 and 14 are pulled, and each of the adhesive parts is stuck to the diaper. Thus the diaper can be disposed of in a rolled state in the same manner as shown in FIG. 15.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An extensible tape comprising a base part and an extensible part linked to said base part, said base part is formed of a material that does not undergo plastic deformation under a load applied in a longitudinal direction of said tape of generally not more than 2000 qf per 25 mm of width of said tape and said extensible Dart is formed of a material that undergoes plastic deformation under a load applied in a longitudinal direction of said tape of generally not more than 2000 qf per 25 mm of width of said tape, said extensible part has a length and a width, the length of said extensible part after stretching is substantially larger than the length of said base part, while the width of said extensible part after stretching is substantially smaller than the width of said base part.

2. The extensible tape of claim 1, wherein said extensible part has an initial length and after plastic deformation, said extensible part has a length substantially 2–10 times the initial length.

3. The extensible tape of claim 2, wherein after plastic deformation said extensible part has a length substantially 4–6 times the initial length.

4. An extensible fastening tape comprising a base part, adapted to be attached to a disposable absorbent article, and an extensible part attached to said base part, said base part is formed of a material that does not undergo plastic deformation under a load applied in a longitudinal direction of said tape of generally not more than 2000 gf per 25 mm of width of said tape and said extensible Dart is formed of a material that undergoes plastic deformation under a load applied in a longitudinal direction of said tape of generally not more than 2000 gf per 25 mm of width of said tape, said extensible part has a length and a width, the length of said extensible part after stretching is substantially larger than the length of said base Dart, while the width of said extensible part after stretching is substantially smaller than the width of said base part, said extensible part being extendable under load to sanitarily contain said disposable absorbent article.

5. The extensible fastening tape according to claim 4, wherein the extensible part extends from both sides of the base part.

6. The extensible fastening tape according to claim 4, wherein two extensible parts extend from the same side of the base part.

7. The extensible fastening tape according to claim 4, wherein the extensible part is folded in layers on itself and on the base part and the folded layers are held together by a releasable adhesive.

8. The extensible fastening tape according to claim 7, wherein an end portion of the extensible part is provided with a fixing part containing a strong adhesive which is adapted for attachment to the disposable absorbent article.

9. The extensible fastening tape of claim 4, wherein said extensible part has an initial length and after plastic deformation, said extensible part has a length substantially 2–10 times the initial length.

10. The extensible fastening tape of claim 9, wherein after plastic deformation said extensible part has a length substantially 4–6 times the initial length.

11. An absorbent article comprising a liquid permeable topsheet, a liquid impermeable backsheet, and an absorbent member interposed between said topsheet and said backsheet, said topsheet or said backsheet being provided with a strip-shaped fastening tape for closing said absorbent article on itself for sanitary disposal after use, at least a portion of said fastening tape being extensible in the longitudinal direction thereof, said fastening tape includes a base part and an extensible part, said base part is formed of a material that does not undergo plastic deformation under a load applied in a longitudinal direction of said tape of generally not more than 2000 gf per 25 mm of width of said tape and said extensible part is formed of a material that undergoes plastic deformation under a load applied in a longitudinal direction of said tape of generally not more than 2000 gf per 25 mm of width of said tape, said extensible part has a length and a width, the length of said extensible part after stretching is substantially larder than the length of said base part, while the width of said extensible part after stretching is substantially smaller than the width of said base part.

12. The absorbent article according to claim 11, wherein said fastening tape includes a fixing part for closing said absorbent article after use, at least a part of said fixing part being extensible in the longitudinal direction of the fastening tape, said fastening tape being folded in the longitudinal direction thereof and fixed to the surface of the topsheet or backsheet at said base part.

13. The absorbent article according to claim 11, wherein said base part is fixed to the surface of the topsheet or backsheet and said extensible part is attached to each end of said base part.

14. The absorbent article according to claim 11, wherein said absorbent article is a disposable diaper.

15. The absorbent article according to claim 11, wherein said absorbent article is a sanitary napkin.

16. The absorbent article of claim 11, wherein said extensible part has an initial length and after plastic deformation, said extensible part has a length substantially 2–10 times the initial length.

17. The absorbent article of claim 16, wherein after plastic deformation said extensible part has a length substantially 4–6 times the initial length.

* * * * *